United States Patent [19]

Sprunt et al.

[11] Patent Number: 5,299,453
[45] Date of Patent: Apr. 5, 1994

[54] METHOD FOR DETERMINING OIL AND WATER SATURATION OF CORE SAMPLES AT OVERBURDEN PRESSURE

[75] Inventors: Eve S. Sprunt, Farmers Branch; Nizar F. Djabbarah, Richardson, both of Tex.

[73] Assignee: Mobil Oil Corporation, Fairfax, Va.

[21] Appl. No.: 10,250

[22] Filed: Jan. 28, 1993

[51] Int. Cl.$^5$ ............... E21B 49/00; G01N 15/08
[52] U.S. Cl. ........................... 73/153; 73/38; 436/31
[58] Field of Search ............ 73/38, 153, 61.43, 61.44, 73/61.59; 436/31, 32, 25

[56] References Cited

U.S. PATENT DOCUMENTS

| | | | |
|---|---|---|---|
| 2,095,056 | 10/1937 | Clough | 73/153 |
| 2,320,681 | 6/1943 | Thompson | 436/31 |
| 2,733,135 | 1/1956 | Huckaby | 436/31 |
| 3,018,660 | 1/1962 | Schmid | 73/153 |
| 4,672,840 | 6/1987 | Cullick | 73/38 |
| 4,787,983 | 11/1988 | DiFoggio et el. | 73/153 |
| 4,920,792 | 5/1990 | DiFoggio | 73/153 |
| 5,114,567 | 5/1992 | DiFoggio | 436/31 |

Primary Examiner—Hezron E. Williams
Assistant Examiner—Michael Brock
Attorney, Agent, or Firm—Alexander J. McKillop; George W. Hager, Jr.; Lawrence O. Miller

[57] ABSTRACT

A method and apparatus is provided to determine the amount of oil and water or brine in a representative core sample of reservoir rock at an overburden stress which approximates reservoir stress conditions. The core sample is initially saturated with reservoir hydrocarbon (crude oil) and aqueous fluids (water or brine). The core sample is surrounded with an elastic jacket, or sleeve, and placed in a confining pressure vessel that simulates reservoir overburden stress on the core sample. The hydrocarbon (oil) fluids and aqueous fluids (water or brine) are than extracted from the core sample with a solvent capable of dissolving both aqueous and hydrocarbon fluids. The solvent and aqueous fluids are separated from the hydrocarbon fluids by evaporation. Thereafter the aqueous fluids are separated from the solvent by extraction. The amounts of oil and aqueous fluids from the sample may be separately determined. The volume of the hydrocarbon fluids and aqueous fluids is determined from their weight and density or from direct volume measurement. For a rock sample fully saturated with a combination of oil and aqueous fluids, the total pore volume is the sum of the volumes of the two fluids and the fluid saturation is then the ratio of the fluid volume to the pore volume.

8 Claims, 2 Drawing Sheets

METHOD FOR DETERMINING OIL AND WATER SATURATION OF CORE SAMPLES AT OVERBURDEN PRESSURE

FIELD OF THE INVENTION

The present invention relates to a method and apparatus for determining the oil and water or brine saturation of a core sample of porous rock taken from a subterranean oil-containing reservoir at overburden stress which approximates reservoir stress conditions.

BACKGROUND OF THE INVENTION

In the drilling of wells, such as oil or gas wells, core samples of porous rock are taken of the earth formation through which the wells are drilled and various characteristics of the rock are determined for the purpose of establishing different fluids in the formation, estimating the quantity of each fluid in the formation, the ease of flow through the formation, etc. Such core samples are also taken from producing reservoirs and characteristics of the rock are determined for the purpose of estimating particular fluid quantities, predicting production rates, etc. Particularly important among the characteristics of the porous rock is determining oil and water saturation and the porosity and permeability of the reservoir.

U.S. Pat. No. 4,920,792 teaches the use of liquified gas extraction to extract oil and brine fluids from a representative porous sample, however, it does not teach determining fluid saturation at an overburden stress which approximates reservoir stress conditions, which is especially important for unconsolidated samples.

It is a specific object of the present invention to provide a new liquified gas extraction method for determining the oil and water saturation of porous core samples at overburden pressure and net stresses representative of those in the reservoir. This new method can be used with consolidated and unconsolidated rock or fractured rock in which pressure-cycling can be a problem. This new method provides separate determination of oil and water or brine saturations, and does not alter rock wettability and causes less damage to clay minerals and gypsum. It is another object of this invention to provide a method that can be used for determining current oil in place and porosity at reservoir pressure without cycling the confining pressure on the formation rock sample. This new method can be readily modified for the determination of solution gas composition, gas-oil ratio (GOR), and oil density and viscosity at reservoir conditions.

SUMMARY

This invention is directed to a method and apparatus for determining the oil and water or brine saturation of a core sample of porous rock taken from a subterranean oil-containing formation at overburden stress which approximates formation stress conditions. The method comprises taking a core sample from the formation which contains an unknown quantity of formation oil and formation brine (or water). The sample is surrounded with an elastic jacket, or sleeve, and placed in a confining pressure vessel. Pressure is applied to the sleeve to press the sleeve into contact with the surface of the core sample. The amount of pressure applied to the sleeve is that amount necessary to simulate the overburden and net stresses on the core sample as specified by the depth of the formation from which the core sample was taken. A solvent capable of dissolving both aqueous and hydrocarbon fluids is injected into the core sample to extract both aqueous and hydrocarbon fluids from the sample. The solvent and aqueous fluid are then separated from the hydrocarbon fluid by evaporation. Thereafter, the aqueous fluid and the solvent are separated by extraction. The amounts of the hydrocarbon (oil) and aqueous fluids may then be separately determined. The apparatus for determining the amount of fluids in a core sample of porous rock comprises: a sleeve containing said core sample of a porous rock saturated with both aqueous and hydrocarbon fluids; means for applying a confining pressure through said sleeve to said core sample; means for regulating the temperature of the core sample within said sleeve; a fluid inlet position in a first end of said sleeve through which a fluid solvent is injected under pressure into a first end of said core sample for extracting both aqueous and hydrocarbon fluids from said sample; a fluid outlet position in a second end of said sleeve through which said solvent and dissolved aqueous and hydrocarbon fluids are discharged from said sample; means for separating said solvent and aqueous fluids from said extracted hydrocarbon fluids; means for determining the amount of said hydrocarbon fluids; means for separating said aqueous fluids from said solvents; and means for determining the amount of separated aqueous and hydrocarbon fluids.

DESCRIPTION OF THE PREFERRED EMBODIMENT

Figure 1:
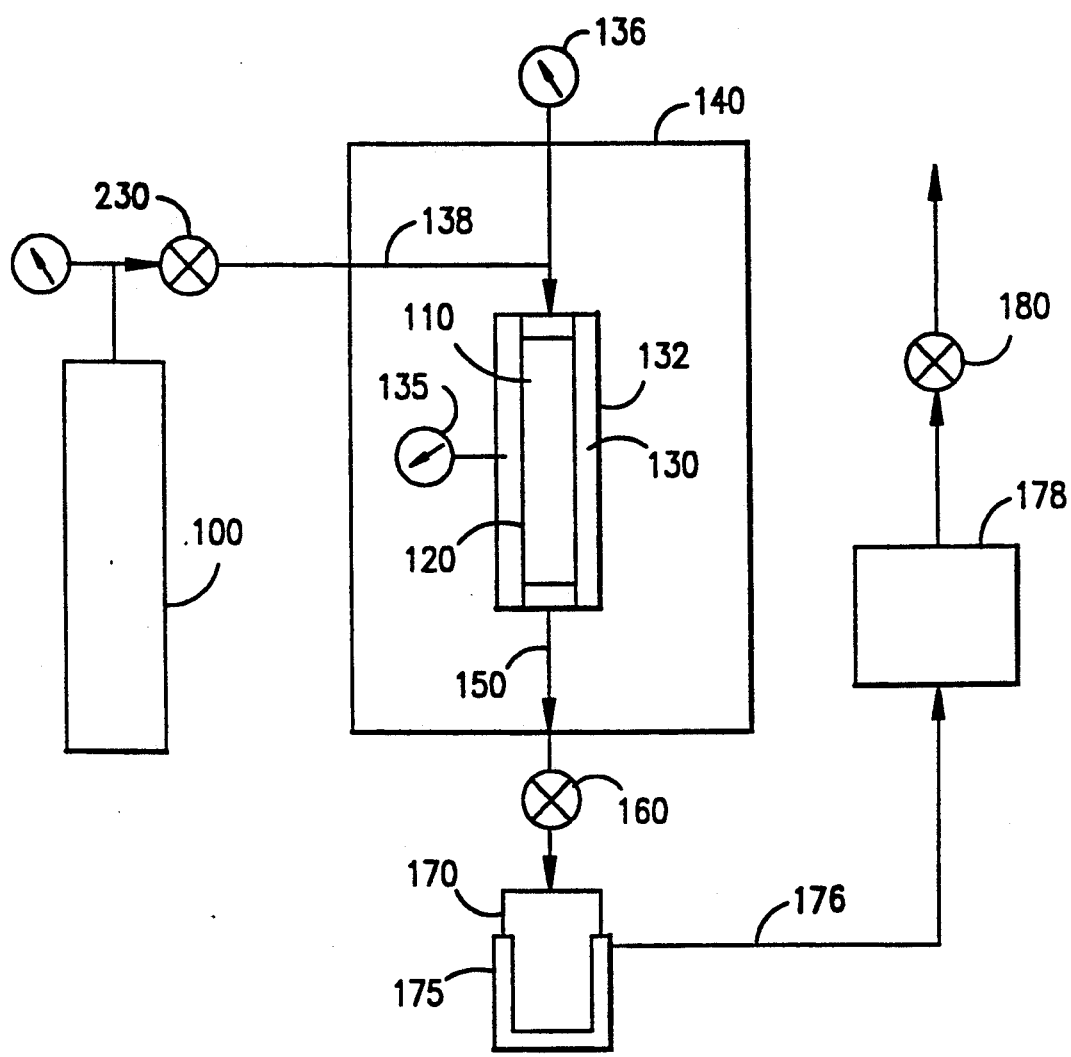
FIG. 1 is a schematic representation of an apparatus for carrying out the method for determination of oil and water saturations in core samples in accordance with the present invention.

Referring now to FIG. 1, there may be seen a partially cross-sectioned view of a gas cylinder 100 which supplies a liquified gaseous solvent at the desired fluid pressure to a representative specimen of a core sample 110 of a porous material, such as a core sample of rock taken from a subsurface oil-containing rock formation. The pressure of the liquified gaseous solvent entering the core sample is measured by a pressure gauge 136. The core sample 110 is mounted in a Hassler core holder 130 and is enclosed within a confining pressure vessel 132 that can be pressurized up to pressures that simulate overburden stress in the formation. The Hassler core holder is described in U.S. Pat. No. 2,345,935, the teaching of which is incorporated herein by reference. The desired confining pressure condition within the vessel 132 is established by the vessel pressure line 135 connected to a pressurizing pump not shown. The core sample 110 is initially saturated with reservoir hydrocarbons (crude oil) and formation aqueous fluids (water or brine). The core sample is surrounded by a jacket, or sleeve, and placed inside a confining pressure vessel 132. Typical of such pressure vessels are those described in U.S. Pat. Nos. 3,839,899 to McMillan; 4,688,238 to Sprunt et al; and 4,379,407 to Masse et al., the teachings of which are incorporated herein by reference. Sufficient confining pressure is applied to the sleeve 120 and hence to the porous core sample 110 to approximate the overburden and net stresses on the core sample of reservoir rock at reservoir stress conditions. The core holder 130 and pressure vessel 132 are placed inside a low-temperature incubator 140.

Liquified gaseous solvent from gas cylinder 100 is injected into the core holder 130 via line 138 at a pressure less than the confining pressure. The temperature of the incubator 140 is low enough to maintain the solvent injected into the core holder 130 in a liquid state at the pore pressure 136. The liquified gaseous solvent flows through the core sample 110 and dissolves both the hydrocarbon and aqueous fluids contained therein and are accordingly carried by the liquified gas solvent to the fluid outlet 150. Both hydrocarbon and aqueous fluids are soluble in the solvent so that any hydrocarbon (oil) trapped in open pore volumes by water, or vice versa is still removed, i.e. extracted, by the solvent.

Figure 2:
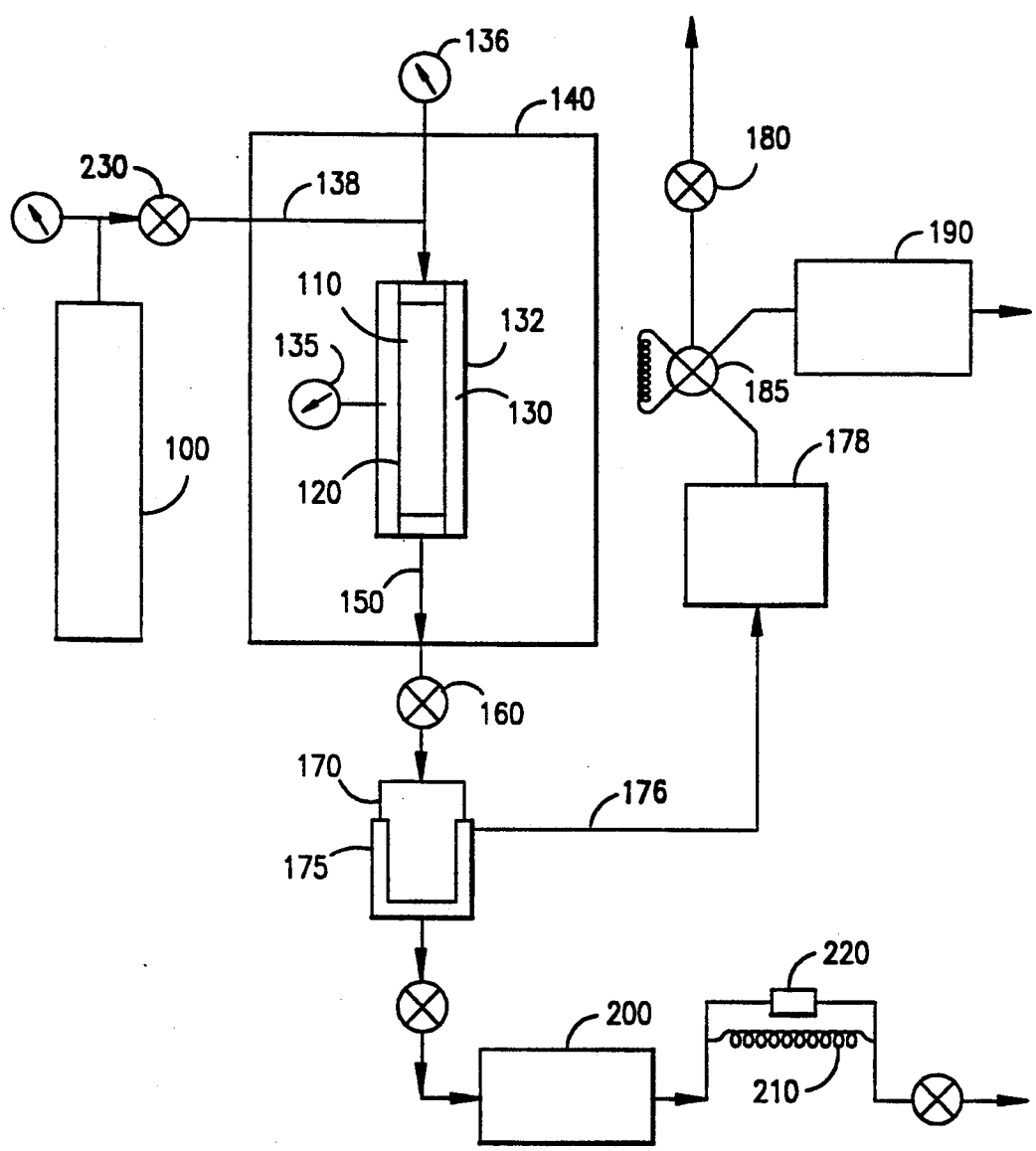
FIG. 2 illustrates a modification of the apparatus shown in FIG. 1 for determination of solution gas composition, gas-oil ratio (GOR), and oil density and viscosity at reservoir conditions.

The liquified gaseous solvent and extracted fluids then flow through a valve-type pressure regulator 160 and then through a gas-liquid separator 170. The gas-liquid separator 170 is maintained at a temperature high enough to vaporize the solvent phase which is azeotroped with the water leaving the hydrocarbon (oil) phase behind in a preweighed container 175. The weight of the hydrocarbon fluids may then be determined. The density of extracted hydrocarbons can be determined after the sample is weighed. If the samples are collected in a container 175 equipped to measure the oil volume acoustically or by other means, then the density may be determined in line as shown in FIG. 2. As shown in FIG. 2, the density of extracted hydrocarbon fluids may be determined by an in-line Mettler-Paar densitometer 200. As shown in FIG. 2, another option would be to install an in-line pressure transducer 220 to determine viscosity of the extracted hydrocarbons (oil). The gaseous solvent-aqueous fluids mixture flows through outlet 176 and into a preweighted anhydrous salt-bed 178 which absorbs the aqueous fluids and allows the solvent to evolve through another pressure release valve 180. The weight of the aqueous fluids (water or brine) may then be determined.

The solvent used to extract the hydrocarbon and aqueous fluids from the core sample must have (1) a low boiling point at atmospheric pressure, (2) be soluble in both a hydrocarbon and aqueous fluid, (3) be safe for handling, i.e. have manageable to no toxicity, (4) have a chemical inertness to rock, brine, and crude oil, (5) form water-gas azeotropic mixtures, and optionally, be capable of dissolving salts.

The solvent may be selected from cycloalkanols, cycloalkenes, cycloalkanes, alkene oxide, methyl amines, and certain freons. Specific examples of such solvents are vinyl chloride, freon R152A, ethylene, clyclopropane, nitrous oxide, diethyl ether, ethyl chloride, propylene, acetylene, and allene. The preferred solvent is cyclopropane. Such solvents may have polar groups, OH groups, or more unsaturated type bonds to help dissolve asphaltenes. Alkyenes have been found to have better water solubility than aromatics.

The above-mentioned solvents are described in U.S. Pat. No. 4,920,792 to DiFoggio and an article entitled "Liquefied-Gas Extraction and Neon-Infrared Analysis of Core", 1991 *Society of Core Analysts Conference*, the teachings of which are incorporated herein by reference.

A wide range of anhydrous salts may be used as bed-packing material in the salt-bed 178. Examples of such salts are sodium carbonate ($Na_2CO_3$), zinc sulfate ($ZnSO_4$), and cupric sulfate ($CuSO_4$). These salts adsorb water molecules and incorporate them in hydrated molecular structure; e.g. sodium carbonate decahydrate ($Na_2CO_3.10H_2O$), zinc sulfate heptahydrate ($CuSO_4.7H_2O$) and cupric sulfate pentahydrate ($CuSO_4.5H_2O$).

The volume of oil in the core is determined by first finding the weight gain of the container in the gas-liquid separator 175 and measuring oil density at the desired conditions of temperature and pressure or from direct measurement of the volume of oil in separator 175. Similarly, the volume of the amount of aqueous fluids is determined from its weigh in the salt-bed 178 and measuring aqueous density at the desired conditions using conventional methods. For a core sample fully saturated with a combination of oil and water, the total pore volume is the sum of the volumes of the two fluids and the fluid saturation is then the ratio of the oil volume to the pore volume, and the water saturation is then the ratio of the water volume to the pore volume.

If the crude oil contains dissolved solution gas below its bubble point, then it is possible to analyze the outlet gas from the salt-bed 178. Referring to FIG. 2, a multi-port sampling valve 185 is used to take a gas sample. The sample is analyzed with a gas chromatograph 190 which can be used to determine dissolved hydrocarbons composition and solution gas-oil ratio (GOR).

Following fluid saturation determination, the core holder 130 is disconnected from the gas-liquid separator 170 at the valve-type back pressure regulator 160 and removed, while still under confining pressure, from the low temperature incubator 140. The pore volume of the core sample 110 can then be determined under confining pressure by disconnecting the liquified gas source 100 at valve source 230 and flooding the core sample with carbon dioxide via line 138 that exits from the sample 110 through line 150. Thereafter the core sample 110 is subjected to a high vacuum through line 138 to withdraw the carbon dioxide. The core sample is then completely saturated with a liquid such as water, brine or a hydrocarbon which is injected into the core sample through line 138 and the pore volume of the core sample is determined from the volume of liquid required to completely saturate the core sample 110. With unconsolidated samples it is particularly important to determine pore volume under confining pressure without disturbing or pressure-cycling the sample. The core sample inside the core holder 130 can then be used for special core analysis tests such as relative permeability without disrupting the sample by pressure cycling or remounting.

Although the present invention has been described with preferred embodiments, it is to be understood that modifications and variations may be utilized without departing from the spirit and scope of this invention, as those skilled in the art will readily understand. Such modifications and variations are considered to be within the purview and scope of the appended claims.

We claim:

1. A method for determining the amount of fluids in a porous sample, comprising:
   (a) providing a representative specimen of porous sample,
   (b) surrounding said sample within an elastic jacket in a confining pressure cell,
   (c) supplying pressure to said cell to pressure said jacket into contact with said sample, (d) extracting both aqueous and hydrocarbon fluids from said sample with a solvent capable of dissolving both aqueous and hydrocarbon fluids, (e) separating said aqueous and hydrocarbon fluids, and (f) determining the amount of aqueous and hydrocarbon fluid from said separated fluids.

2. A method of claim 1 wherein said solvent comprises cyclopropane, vinyl chloride, freon R152A, or mixtures thereof.

3. A method of claim 1 wherein the sample is obtained from a subterranean porous rock formation and the pressure applied to said jacket is equal to the overburden pressure and net stresses on the sample at reservoir stress conditions.

4. A method of claim 1, further comprising the step of determining the density of the extracted hydrocarbon fluid and aqueous fluid.

5. A method of claim 1, further comprising the step of determining the pore volume of said sample without pressure-cycling the confining pressure applied to said sample.

6. A method for determining the amount of fluids in a porous sample containing aqueous and hydrocarbon fluids, comprising:

(a) surrounding said sample within an elastic jacket in a confining pressure cell, (b) supplying pressure to said cell to pressure said jacket into contact with said sample, (c) extracting said sample with a solvent capable of dissolving both aqueous and hydrocarbon fluids to remove said aqueous and hydrocarbon fluids from said sample, (d) separating said solvent and aqueous fluids from said extracted hydrocarbon fluids by evaporation, (e) separating said aqueous fluids from said solvent, and (f) determining the volumes of said extracted hydrocarbon fluid and said separated aqueous fluid.

7. A method of claim 6 wherein said solvent comprises cyclopropane, vinyl chloride, freon R152A, or mixtures thereof.

8. A method of claim 6, further comprising the step of determining pore volume of said sample without pressure-cycling the confining pressure applied to said sample.

* * * * *